United States Patent
Ebisawa

(10) Patent No.: US 9,535,159 B2
(45) Date of Patent: Jan. 3, 2017

(54) TEST-OBJECT-INFORMATION ACQUISITION APPARATUS AND TEST-OBJECT-INFORMATION ACQUISITION METHOD

(71) Applicant: CANON KABUSHIKI KAISHA, Tokyo (JP)

(72) Inventor: Hisafumi Ebisawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 614 days.

(21) Appl. No.: 13/905,014

(22) Filed: May 29, 2013

(65) Prior Publication Data
US 2013/0322204 A1    Dec. 5, 2013

(30) Foreign Application Priority Data
Jun. 1, 2012    (JP) ................ 2012-126381

(51) Int. Cl.
*G01S 15/89* (2006.01)
*A61B 8/00* (2006.01)
(Continued)

(52) U.S. Cl.
CPC ......... *G01S 15/8965* (2013.01); *A61B 5/0095* (2013.01); *A61B 8/4209* (2013.01);
(Continued)

(58) Field of Classification Search
CPC ... A61B 5/0095; A61B 8/4209; A61B 8/4461; A61B 8/4483; A61B 8/463; A61B 8/5207; A61B 8/5246; A61B 8/5261; A61B 8/00; A61B 8/08; G01N 2291/02475; G01N 2291/02483; G01N 29/0654; G01N 29/2418; G01N 29/265; G01N 29/44; G01N 29/06; G01N 29/24; G01S 15/89
(Continued)

(56) References Cited

U.S. PATENT DOCUMENTS 5,097,709 A * 3/1992 Masuzawa ............ B06B 1/0629
                                                         310/334
6,166,373 A * 12/2000 Mao ..................... G01C 11/025
                                                         250/226
(Continued)

FOREIGN PATENT DOCUMENTS

| CN | 1575770 A | 2/2005 |
| CN | 101352354 A | 1/2009 |

(Continued)

*Primary Examiner* — Isam Alsomiri
*Assistant Examiner* — Amienatta M Ndure Jobe
(74) *Attorney, Agent, or Firm* — Canon USA Inc., IP Division

(57) ABSTRACT

A test-object-information acquisition apparatus includes a light radiating unit, a first probe that receives an acoustic wave generated in a test object in response to the test object being irradiated with light radiated by the light radiating unit, a second probe that radiates an ultrasound beam towards the test object and receives a reflected wave from the test object, an ultrasound controller configured to control the second probe, and a scanning unit configured to cause the light radiating unit and the first and second probes to perform a reciprocating scan process across the test object. The ultrasound controller varies a radiation method for radiating the ultrasound beam from the second probe to the test object so that the radiation method is different between an outbound scan and a return scan of the reciprocating scan process.

17 Claims, 6 Drawing Sheets

(51) Int. Cl.
*A61B 5/00* (2006.01)
*G01N 29/06* (2006.01)
*G01N 29/24* (2006.01)
*G01N 29/265* (2006.01)
*G01N 29/44* (2006.01)
*A61B 8/08* (2006.01)

(52) U.S. Cl.
CPC ....... *A61B 8/5246* (2013.01); *G01N 29/0654* (2013.01); *G01N 29/2418* (2013.01); *G01N 29/265* (2013.01); *G01N 29/44* (2013.01); *A61B 8/4461* (2013.01); *A61B 8/4483* (2013.01); *A61B 8/463* (2013.01); *A61B 8/5207* (2013.01); *G01N 2291/02475* (2013.01); *G01N 2291/02483* (2013.01)

(58) Field of Classification Search
USPC ............................................................ 367/7
See application file for complete search history.

(56) References Cited

U.S. PATENT DOCUMENTS

| 2009/0187099 A1* | 7/2009 | Burcher ............... A61B 5/0059 600/430 |
| 2010/0094134 A1 | 4/2010 | Zhu et al. |
| 2011/0066023 A1* | 3/2011 | Kanayama ........... A61B 5/0091 600/407 |

FOREIGN PATENT DOCUMENTS

| JP | 6196460 A | 5/1986 | |
| JP | 2003-019132 A | 1/2003 | |
| JP | 2009-131420 A | 6/2009 | |
| JP | 2010-022816 A | 2/2010 | |
| JP | 2010022812 A | 2/2010 | |
| JP | 2010164764 A * | 7/2010 | ............. G03G 15/00 |
| JP | 2010-167257 A | 8/2010 | |
| JP | 2011-172730 A | 9/2011 | |

* cited by examiner

TEST-OBJECT-INFORMATION ACQUISITION APPARATUS AND TEST-OBJECT-INFORMATION ACQUISITION METHOD

BACKGROUND OF THE INVENTION

Field of the Invention

The present invention relates to test-object-information acquisition apparatuses and test-object-information acquisition methods.

Description of the Related Art

Diagnostic apparatuses, such as diagnostic ultrasound apparatuses and photoacoustic imaging apparatuses (diagnostic photoacoustic apparatuses), are well known. Because such diagnostic apparatuses are not involved with X-ray radiation, these apparatuses are attracting attention as safe diagnostic apparatuses with no risk of radiation exposure. Japanese Patent Application Laid-Open No. 2010-22812 discusses a test-object-information acquisition apparatus as an example of such a diagnostic apparatus. This test-object-information acquisition apparatus causes a light source, a photoacoustic probe, and an ultrasound probe to scan across an image capture area on a test object so as to create a photoacoustic image and an ultrasound image over a wide area and to superimpose the two images onto each other.

In the apparatus discussed in Japanese Patent Application Laid-Open No. 2010-22812, the information of the test object is acquired while the probes scan across the test object. However, since the method for acquiring the test-object information varies between the photoacoustic image and the ultrasound image, the information obtained from the two images is often inconsistent.

SUMMARY OF THE INVENTION

One aspect of the present invention is directed to a test-object-information acquisition apparatus including a light radiating unit configured to radiate light onto a test object; a first probe that receives an acoustic wave generated in the test object in response to the test object being irradiated with the light from the light radiating unit and converts the acoustic wave into a first electric signal; a second probe that radiates an ultrasound beam towards the test object, receives a reflected wave of the ultrasound beam from the test object, and converts the reflected wave into a second electric signal; an ultrasound controller configured to control the second probe to radiate the ultrasound beam toward the test object; a scanning unit configured to cause the light radiating unit, the first probe, and the second probe to perform a reciprocating scan process across the test object; a photoacoustic-image acquisition unit configured to acquire a photoacoustic image on the basis of the first electric signal; an ultrasound-image acquisition unit configured to acquire an ultrasound image on the basis of the second electric signal; and a controller configured to cause a display unit to display the acquired photoacoustic image and the acquired ultrasound image. The ultrasound controller varies a radiation method for radiating the ultrasound beam from the second probe to the test object so that the radiation method is different between an outbound scan and a return scan of the reciprocating scan process.

Further features of the present invention will become apparent from the following description of exemplary embodiments with reference to the attached drawings.

DESCRIPTION OF THE EMBODIMENTS

Figure 1:
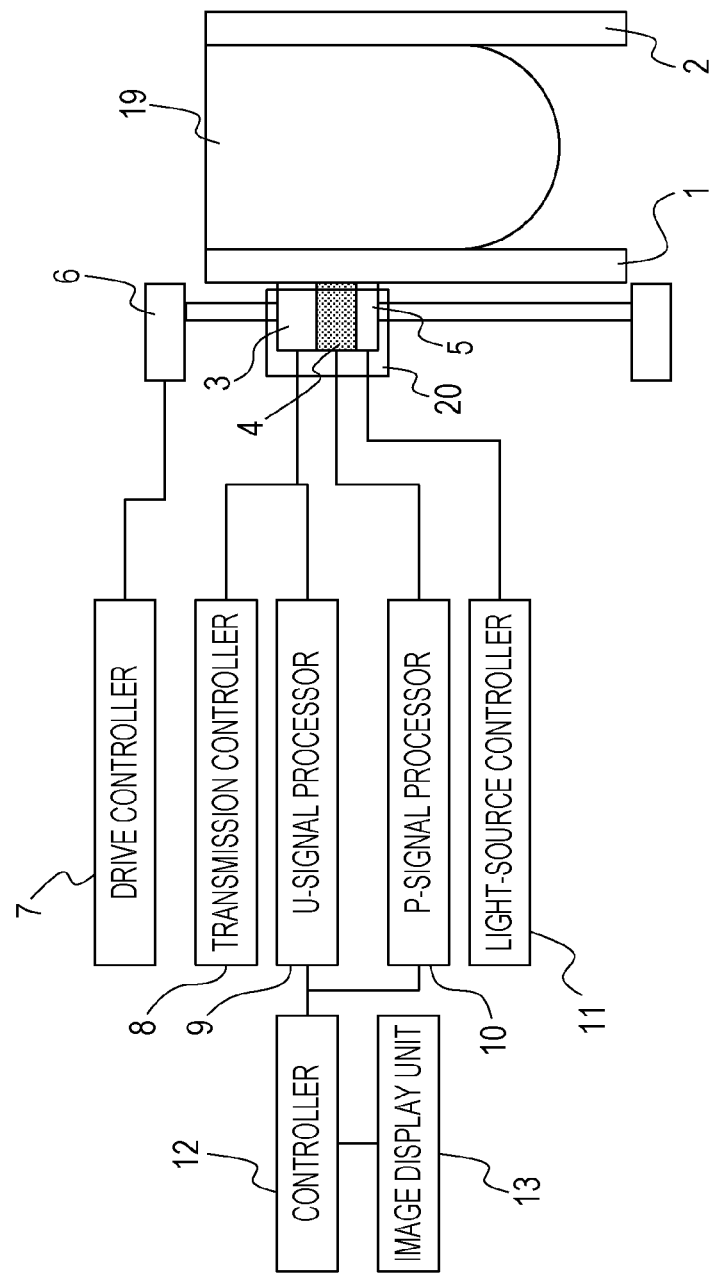
FIG. 1 illustrates the configuration of a test-object-information acquisition apparatus according to an embodiment of the present invention.

An embodiment of the present invention will now be described with reference to the drawings. FIG. 1 schematically illustrates the configuration of a test-object-information acquisition apparatus according to this embodiment. The test-object-information acquisition apparatus according to this embodiment includes a light source 5 serving as a light radiating unit that radiates light to a test object 19, and a photoacoustic probe 4 serving as a first probe that receives an acoustic wave generated in the test object 19 irradiated with the light from the light source 5 and converts the acoustic wave into a first electric signal. The test-object-information acquisition apparatus also includes an ultrasound probe 3 serving as a second probe that radiates ultrasound towards the test object 19, receives a reflected wave of the ultrasound from the test object 19, and converts the reflected wave into a second electric signal; and a transmission controller 8 serving an ultrasound controller that controls the radiation of the ultrasound toward the test object 19 by the second probe. In this embodiment, the light source 5, the photoacoustic probe 4, and the ultrasound probe 3 are preferably secured to and integrated in a carriage 20. Furthermore, the test-object-information acquisition apparatus includes a driving mechanism 6 and a drive controller 7 that constitute a scanning unit that causes the carriage 20, having the light source 5, the photoacoustic probe 4, and the ultrasound probe 3 secured thereto, to scan back and forth across the test object 19 in a reciprocating manner. The test-object-information acquisition apparatus further includes a P-signal processor 10 serving as a photoacoustic-image acquisition unit that acquires a photoacoustic image on the basis of the first electric signal converted from the photoacoustic wave, and a U-signal processor 9 serving as an ultrasound-image acquisition unit that acquires an ultrasound image on the basis of the second electric signal converted from the reflected wave of the ultrasound. Moreover, the test-object-information acquisition apparatus includes a controller 12 that causes an image display unit 13 serving as a display unit to display the acquired photoacoustic image and the acquired ultrasound image. When performing the reciprocating scan process in which the carriage 20 scans back and forth across the test object 19 in a reciprocating manner, the transmission controller 8 serving as an ultrasound controller makes the ultrasound probe 3 serving as a second probe radiate ultrasound towards the test object 19 based on different radiation methods between the outbound scan and the return scan of the reciprocating scan process. Thus, the consistency between the photoacoustic image and the ultrasound image is improved. This will be described below.

Figure 4A:
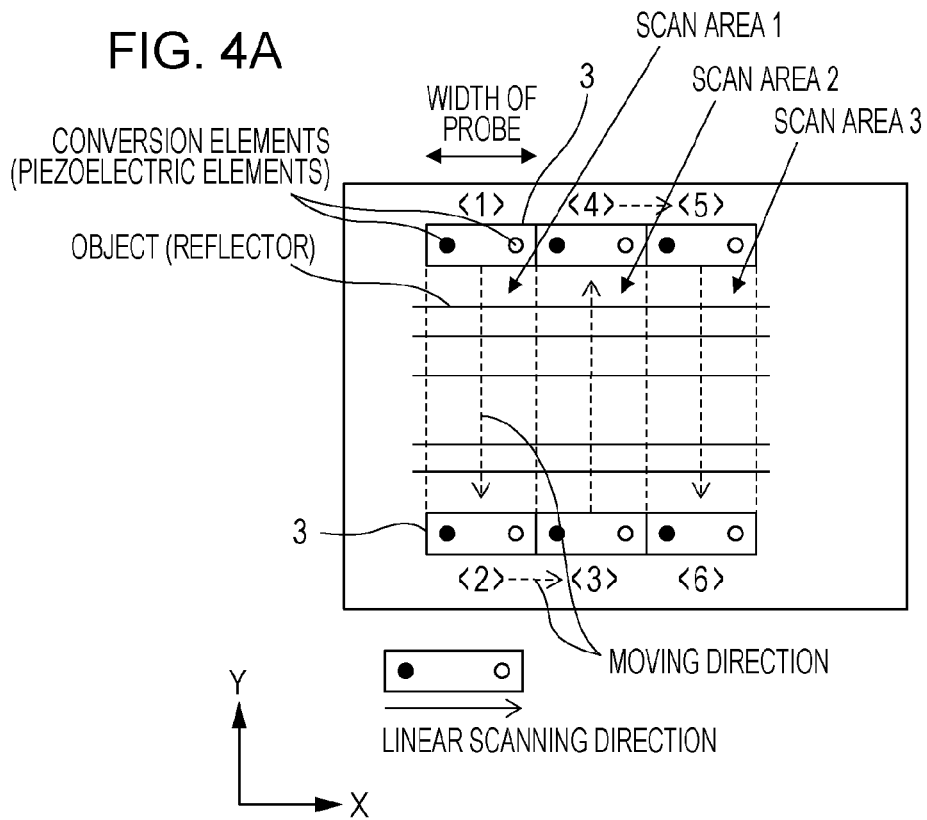
FIGS. 4A and 4B illustrate a method for driving an ultrasound-image acquisition unit and problems therein.
Figure 4B:
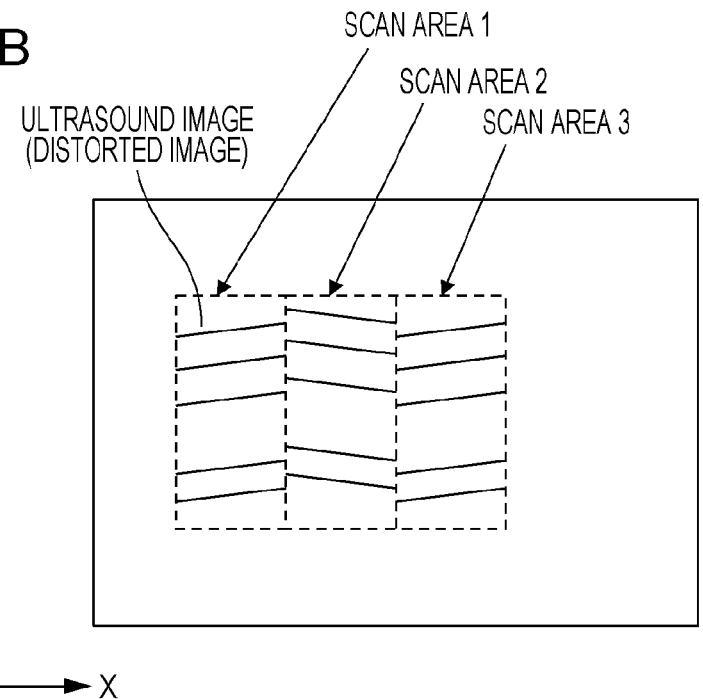

FIGS. 4A and 4B schematically illustrate the reciprocating scan process of the ultrasound probe 3 and an ultrasound image acquired without using the embodiment of the present invention. In FIG. 4A, a plurality of linear objects (i.e., objects that generate an acoustic wave by absorbing light and that reflect ultrasound, such as an imitation of a tumor) are disposed within a test-object scan area. In FIG. 4A, numerals enclosed in angular brackets, such as <1>, <2>, <3> . . . <n> denote the scanning order. To that end, the carriage 20 to which the ultrasound probe 3 is secured performs a scan in the order indicated by the bracketed numbers in the direction of "MOVING DIRECTION" arrows from a first position <1> toward a final position <n>. In FIG. 4A, only positions <1>, <2> . . . to final position <6> are shown for simplicity of illustration, but several more scanning positions may be sequentially scanned. For illustrative purposes, only the ultrasound probe 3 in the carriage 20 is shown in FIG. 4A. The black and white dots in the ultrasound probe 3 denote conversion elements (vibrating elements), which are of the same type but are shown in different colors to clearly show the positional relationships of the end of the probe among position <1> to position <6>.

In order to obtain wide-range information by sequentially moving the focal position of an ultrasound beam within the test object 19 while driving multiple conversion elements at the same time, a so-called linear scan (i.e., scanning of an ultrasound transmission beam in the positive direction of the X-axis in FIGS. 4A and 4B) is performed so as to radiate ultrasound and receive a reflected wave from the test object in response to the radiated ultrasound. Specifically, by radiating the ultrasound multiple times from the start to the end of the linear scan, information is obtained from multiple locations in the X direction. When the ultrasound probe 3 performs a scan from position <1> to position <2> (an outbound scan), a linear scan is performed. Since the ultrasound probe 3 is scanning across the test object 19 along the Y-axis during this linear scan, the acquired ultrasound image is an image that is distorted in the combined direction of the linear scanning direction (X direction) and the scanning direction of the ultrasound probe 3 (Y direction), as shown in a scan area 1, which is an area between position <1> and position <2>, in FIG. 4B. This distortion occurs because the position of the ultrasound probe 3 relative to the test object 19 is different between the start and the end of the linear scan.

Subsequently, while the ultrasound probe 3 performs a scan from position <3> to position <4> (a return scan) without changing the linear scanning direction, ultrasound is radiated to the test object 19 and a reflected wave of the ultrasound is received. The acquired ultrasound image in this case is shown in a scan area 2, which is an area between position <3> and position <4>, in FIG. 4B and is an image that is distorted in a direction that is different to that of the image in the scan area 1. Accordingly, differently distorted images are acquired in the outbound scan and the return scan of the ultrasound probe 3. On the other hand, a photoacoustic image is acquired by obtaining test-object information simultaneously from multiple locations (i.e., a wide range) of the test object 19 in one light radiation process. Thus, distortion as in an ultrasound image does not occur in a photoacoustic image. Therefore, the consistency between an ultrasound image and a photoacoustic image, even when these formed images correspond to the same area, needs to be addressed.

In this embodiment, the method for radiating ultrasound to the test object 19 is varied between the outbound scan and the return scan of the reciprocating ultrasound probe 3. Specifically, although this embodiment includes a step of acquiring a photoacoustic image by radiating light to the test object 19 while scanning the light back and forth across the test object 19 in a reciprocating manner and then receiving an acoustic wave from the test object 19, and a step of acquiring an ultrasound image by radiating ultrasound to the test object 19 while scanning the ultrasound back and forth across the test object 19 in a reciprocating manner and then receiving a reflected wave of this ultrasound from the test object 19, the radiation method for radiating the ultrasound to the test object 19 while scanning the ultrasound back and forth across the test object 19 in a reciprocating manner is different between the outbound scan and the return scan. Specifically, the linear scanning direction is different between the outbound scan and the return scan. More specifically, when linearly-scanning the ultrasound radiated from the plurality of conversion elements arranged in a first direction of the ultrasound probe 3, the radiation method is varied so that the linear scanning direction is different between the outbound scan and the return scan. The first direction in this case is the X direction in FIG. 4A.

Alternatively, the ultrasound may be radiated to the test object 19 only during the outbound scan or the return scan. More specifically, the reciprocating scan process may be performed such that the scan areas at least partially overlap in the outbound scan and the return scan, and the radiation method may be varied so that the ultrasound is radiated to the test object 19 only during the outbound scan or the return scan. Accordingly, the distorting direction of an ultrasound image can be made uniform between areas corresponding to the outbound scan (i.e., the scan areas 1 and 3 in FIG. 4A) and an area corresponding to the return scan (i.e., the scan area 2 in FIG. 4A) in the reciprocating scan process, so that differences in distortion among the areas of the ultrasound image, as described above, are suppressed, whereby the consistency between the ultrasound image and the photoacoustic image is improved.

Next, the components included in the apparatus according to this embodiment will be described.

The light source 5 serving as a light radiating unit is capable of emitting pulsed light in the order of nanoseconds with a specific wavelength, and is, for example, a pulse laser that can emit pulsed light with a wavelength ranging between 600 nm and 1500 nm. Specific examples include a solid laser, a gas laser, a dye laser, and a semiconductor laser. Alternatively, a light-emitting diode or the like may be used. The operation of the light source 5 is controlled by a light-source controller 11. Specifically, the light-source controller 11 controls the quantity of light to be radiated and the radiation timing. The photoacoustic probe 4 serving as a first probe and the ultrasound probe 3 serving as a second probe desirably receive a photoacoustic wave generated in the test object 19 having absorbed light and then convert the photoacoustic wave into an electric signal, or transmit ultrasound to the test object 19 and receive a reflected wave of the ultrasound from the test object 19 and then convert the reflected wave into an electric signal. In order to achieve this, the photoacoustic probe 4 and the ultrasound probe 3 are each constituted of a plurality of conversion elements (vibrating elements) composed of, for example, a piezoelectric ceramic material typified by lead zirconate titanate (PZT) suitable for detecting an elastic wave ranging between 0.5 MHz and several tens of MHz, or a piezoelectric polymer film material typified by polyvinylidene fluoride (PVDF). Alternatively, capacitance-type conversion elements may be used, which are preferably applied to this embodiment of the present invention since they particularly have a wide operating frequency range. The transmission controller 8 serving as an ultrasound controller is configured to control the ultrasound transmission operation of the ultrasound probe 3, and performs on-off control of the ultrasound transmission operation and controls the driving timing of the ultrasound probe 3 for focusing the transmitted ultrasound onto an arbitrary position of the test object 19. Specifically, the transmission controller 8 controls the delay time for a signal that drives each of the vibrating elements included in the ultrasound probe 3. Consequently, the transmission controller 8 also controls the linear scan described above. The driving mechanism 6 constituting the scanning unit is configured to cause the carriage 20 to scan back and forth across the test object 19 in a reciprocating manner along the surface of a support member 1, to be described later, and may be constituted of, for example, a combination of a pulse motor and a ball screw, or a linear motor. The operation of the driving mechanism 6 is controlled by the drive controller 7 that constitutes the scanning unit together with the driving mechanism 6. The U-signal processor 9 serving as an ultrasound-image acquisition unit will be described in detail later with reference to FIG. 2. The controller 12 is configured to perform control for making the image display unit 13 display the photoacoustic image and the ultrasound image acquired by the P-signal processor 10 and the U-signal processor 9, and performs, for example, control for combining the two images.

The embodiment shown in FIG. 1 preferably includes the support member 1, a support member 2, and the image display unit 13. This will be described below.

The support members 1 and 2 support the test object 19 so as to prevent the test object 19 from moving during a measurement process. In the embodiment shown in FIG. 1, the support members 1 and 2 are formed of a pair of substantially parallel plates, but other configurations such as symmetric curved plates may also be feasible. With the appropriate design of support members 1 and 2, the test object 19 can be held securely in an appropriate imaging position without moving. Thus, a higher-precision photoacoustic image and a higher-precision ultrasound image can be acquired. The support member 1 is preferably composed of a material with high transmission properties for light emitted from the light source 5 as well as for an acoustic wave generated in the test object 19 and for ultrasound emitted from the ultrasound probe 3. Examples of such a material include quartz glass, polymethylpentene polymer, polycarbonate, and acrylic. The support member 1 may have a thickness ranging between about 3 mm and 10 mm; the precise thickness may be established in view of a tolerable attenuation of the acoustic wave, and enough mechanical strength necessary for securely supporting the test object 19. The image display unit 13 is configured to display the photoacoustic image and the ultrasound image on the basis of image signals transmitted from the controller 12, and may be an already-existing display device, such as a liquid-crystal display, a plasma display, an organic electroluminescence (EL) display, or a field emission display (FED).

Next, the U-signal processor 9 will be described with reference to FIG. 2.

Figure 2:
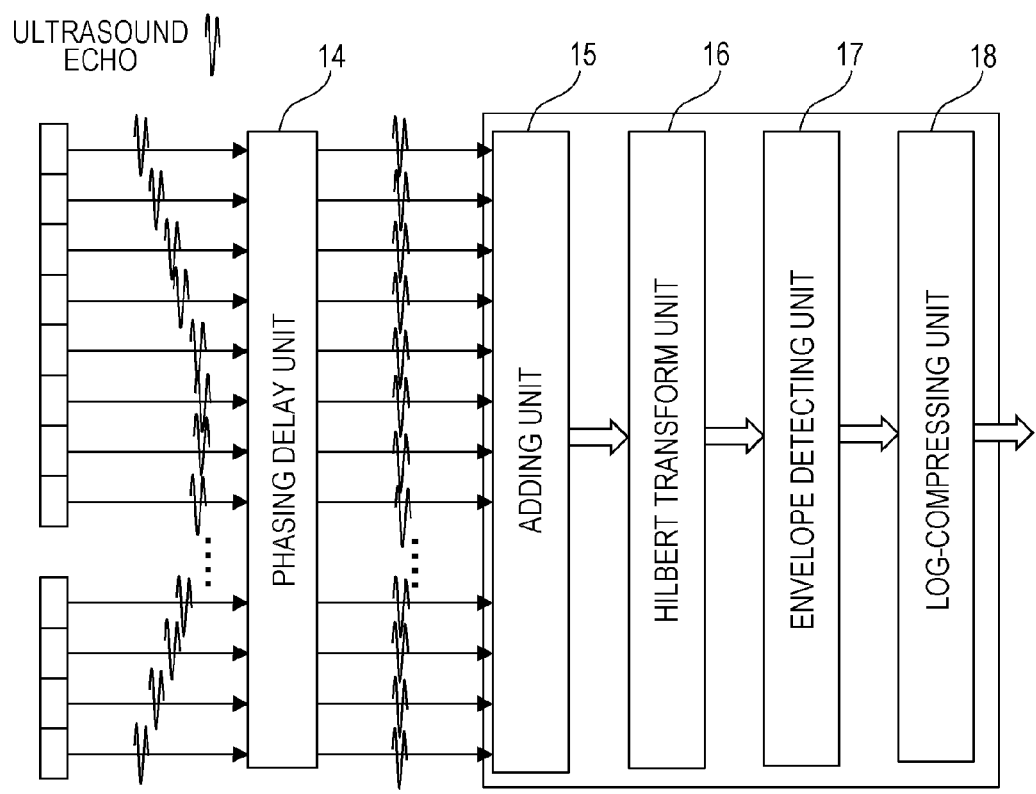
FIG. 2 illustrates the configuration of a U-signal processor according to the embodiment of the present invention.

FIG. 2 illustrates the configuration of the U-signal processor 9. As shown in FIG. 2, the U-signal processor 9 includes a phasing delay unit 14, an adding unit 15, a Hilbert transform unit 16, an envelope detecting unit 17, and a log-compressing unit 18. The phasing delay unit 14 delays signals (i.e., ultrasound signals) received by the conversion elements so as to align the phases of the signals. In this embodiment, piezoelectric elements are used as an example of the vibrating elements. The adding unit 15 adds the delayed signals together. The Hilbert transform unit 16 performs Hilbert transform on the combined signal, and the envelope detecting unit 17 detects the signal having undergone the Hilbert transform. The log-compressing unit 18 performs log-compression on the detected signal.

When ultrasound is transmitted toward the test object 19, the transmitted ultrasound is reflected and scattered by the test object 19 and returns to the vibrating elements as an ultrasound echo (reflected wave). A group of vibrating elements that form a reception opening each convert the ultrasound echo (reflected wave) into an electric signal (second electric signal), which is acquired as a received signal.

The received signals are transmitted to the U-signal processor 9 so that an image is acquired (re-formed) in the U-signal processor 9. The procedure of this process will be described below.

First, the phasing delay unit 14 determines a delay time for the received signal of each vibrating element on the basis of depth information and performs delay processing on each received signal. The delay time is determined in view of the structure of the ultrasound probe 3 and the acoustic properties of the test object 19, in addition to the thickness and the acoustic properties of the support member 1.

The received signals having undergone the delay processing are added together in the adding unit 15. Subsequently, the combined signal undergoes Hilbert transform and envelope detection at the Hilbert transform unit 16 and the envelope detecting unit 17, whereby an image is re-formed (acquired). Although the processing technique used in the U-signal processor 9 in this case is a phasing-and-adding technique used in a general diagnostic ultrasound apparatus, a re-forming technique such as adaptive signal processing is also effective. The re-formed (acquired) image data is log-compressed by the log-compressing unit 18 so as to become image data equivalent to one line. By performing a series of processing while moving the scan line, a two-dimensional ultrasound image extending in the linear scanning direction is created.

Next, a procedure for forming an image from an acoustic wave will be described below.

First, pulsed light is radiated to the test object 19 from the light source 5. The light radiated from the light source 5 propagates through and is absorbed by the test object 19. For example, if the test object 19 is a biological organism, the light is specifically absorbed by the blood and the blood vessels within the biological organism, whereby an acoustic wave is generated by thermal expansion. If the biological organism has cancer, the light is specifically absorbed by new blood vessels of the cancer cells, as in the other blood vessels, whereby an acoustic wave is generated.

The acoustic wave reaches each of the vibrating elements constituting the photoacoustic probe 4, where the acoustic wave is converted into an analog electric signal (first electric signal).

The analog signal from each vibrating element is converted into a digital signal by the P-signal processor 10, whereby image data is re-formed (acquired).

The ultrasound image and the photoacoustic image respectively re-formed (acquired) by the U-signal processor 9 and the P-signal processor 10 are superimposed on each other by the controller 12. In addition to superimposing the two images on each other while aligning the positions thereof with each other, the two images can be displayed as individual images or may be displayed side-by-side, depending on the conditions.

The image display unit 13 displays the image data combined at the controller 12. This series of steps is performed while making the ultrasound probe 3, the photoacoustic probe 4, and the light source 5 scan across the test object 19 so that three-dimensional image data of the entire test object 19 can be acquired. Next, the scan process (i.e., reciprocating scan process) will be described below with reference to FIGS. 3A to 3C.

Figure 3A:
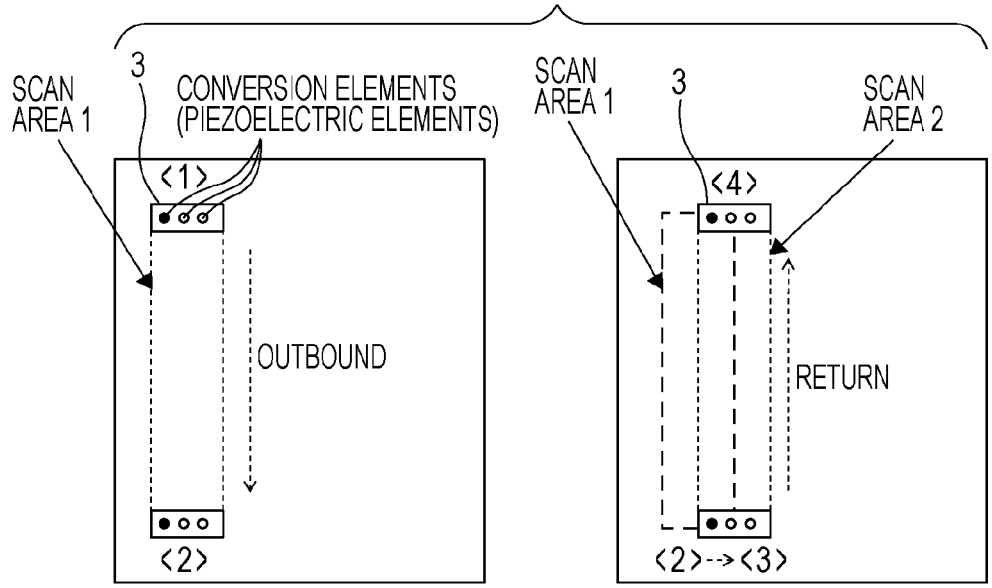
FIGS. 3A, 3B and 3C illustrate a procedure for forming an image of an entire image capture area according to the embodiment of the present invention.
Figure 3B:
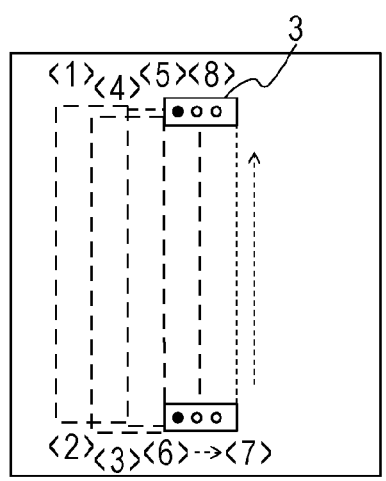
Figure 3C:
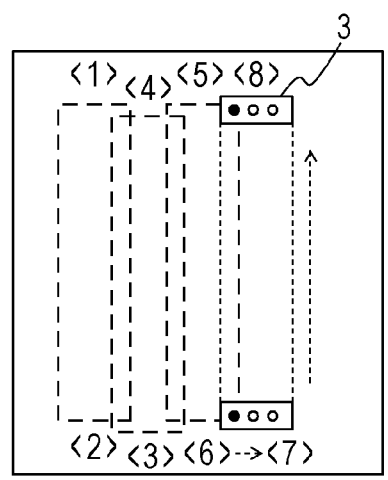

When an area to be image-captured is determined, the probes are scanned across the test object 19 so that the probes travel throughout the entire area thereof. During the scan, the probes receive an acoustic wave and an echo (reflected wave) of ultrasound radiated toward the test object 19, so that images are formed. As shown in FIG. 3A, the carriage 20 is first moved from position <1> toward position <2> (outbound scan). For illustrative purposes, only the ultrasound probe 3 secured to the carriage 20 is shown. During this time, the ultrasound echo (reflected wave) and the photoacoustic wave are received separately at different timings so as to prevent them from interfering with each other. After the carriage 20 is moved to an edge (position <2>) of the image capture area, the carriage 20 slides to position <3>. Then, while the carriage 20 is moved toward position <4> (return scan), an ultrasound echo (reflected wave) and an acoustic wave are received. In this case, the ultrasound radiation method is different between the outbound scan and the return scan, as described above. Furthermore, the sliding distance (i.e., sliding distance from position <2> to position <3> in the positive direction of the X-axis) in this case can be arbitrarily changed, as shown in FIGS. 3B and 3C. The amount of overlap between image scan areas varies between the outbound scan and the return scan depending on the sliding distance. Since the reference data at the time of image re-formation increases with an increasing number of overlapping regions, the signal-to-noise (S/N) ratio of each received signal is improved. Therefore, if the processing time required for a single re-formation process is fixed, the reciprocating scan process shown in FIG. 3C contributes to a shorter image-capturing time but a lower S/N ratio, as compared with the reciprocating scan process shown in FIG. 3B, resulting in image degradation. Although the scan area between position <3> and position <4> is displaced in the Y direction in FIGS. 3B and 3C so as to provide a better illustration of how the scan areas overlap, the scan areas are aligned with each other in actuality. By repeating the reciprocating scan process from position <1> to position <8> in this manner, the probes are moved throughout the entire area to be image-captured, thereby completing the scan process. Although the reciprocating scan process is performed such that the scan areas partially overlap between the outbound scan and the return scan, as described above, the reciprocating scan process may alternatively be performed such that the scan areas are the same between the outbound scan and the return scan, that is, the scan areas completely overlap, or such that the scan areas do not overlap at all between the outbound scan and the return scan. Furthermore, although each probe moves sequentially from one side of a movement path thereof, a different movement path is permissible so long as the probe moves across the entire area to be image-captured and a required S/N ratio is ensured.

The present invention will be described below in detail with reference to specific examples.

First Example

FIG. 1 schematically illustrates a test-object-information acquisition apparatus according to a first example.

First, the configuration for acquiring an ultrasound image from the test object 19 will be described. The ultrasound probe 3 is a 128-channel linear probe having conversion elements formed of 128 piezoelectric elements arranged in an array. The piezoelectric elements are composed of PZT having a center frequency of 6 MHz. The support member 1 supporting the test object 19 is a 7-mm-thick resin plate composed of polymethylpentene. The support member 2 is a 10-mm-thick acrylic-resin plate. The transmission controller 8 sends an electric signal to each piezoelectric element; and in response, the array of piezoelectric elements forms a transmission beam at a target focal position of the test object 19. Specifically, in response to an operation of the transmission controller 8, each piezoelectric element converts the electric signal into an ultrasound signal; then the ultrasound signal is transmitted to a target focal position of the test object 19. The transmitted ultrasound is subsequently reflected and scattered by the test object 19. The reflected signal (an ultrasound echo) returns to a plurality of piezoelectric elements, which form a reception opening. Since, in the first example, the reception opening is formed by a group of 64 (64-ch) piezoelectric elements, data collected along a scan line include 64 received signals. The data corresponding to the received signals are transmitted to the U-signal processor 9. In the U-signal processor 9, the image data along the scan line is re-formed (acquired).

Next, the configuration for acquiring a photoacoustic image will be described. The light source 5 is a titanium-sapphire laser, which is a type of a solid laser. The wavelength of the titanium-sapphire laser can be tunable, and in this example is set to 750 nm. The light source 5 (titanium-sapphire laser) is controlled by the light-source controller 11 and emits light at intervals of 10 Hz. Pulsed light is radiated from the light source 5, and an acoustic wave generated within the test object 19 is detected by the photoacoustic probe 4. The photoacoustic probe 4 includes 600 (20×30) piezoelectric elements in a 2 mm by 2 mm area and is formed so as to have a center frequency of 2 MHz. The acoustic wave is converted into an analog electric signal in each piezoelectric element. The analog signals are transmitted to the P-signal processor 10, whereby image data is acquired (re-formed) in the P-signal processor 10.

Next, the reciprocating scan process of each probe will be described.

The ultrasound probe 3, the photoacoustic probe 4, and the light source 5 are packaged in a single carriage 20, which is disposed on the driving mechanism 6. When an image capture area is set, the drive controller 7 drives the motor that constitutes the driving mechanism 6 so as to move the carriage 20. In the first example, the motor is a pulse motor. The carriage 20 can be moved at an arbitrary speed to an arbitrary position in two axial directions by the driving mechanism 6 constituted of a combination of the pulse motor and a ball screw. The carriage 20 scans back and forth across the test object 19 in a reciprocating manner such that the outbound paths and the return paths partially overlap and that the outbound paths arranged side-by-side have no gaps therebetween, as shown in FIG. 3B. This allows for an improved signal-to-noise (S/N) ratio, thereby achieving a high-definition photoacoustic image.

Figure 6A:
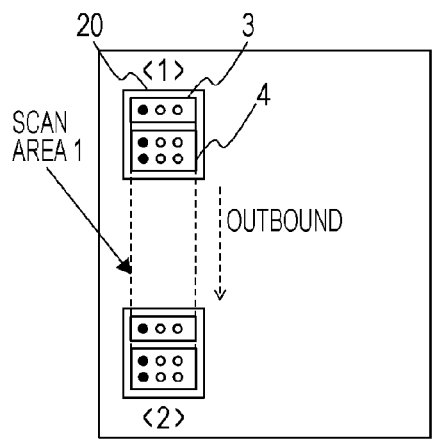
FIGS. 6A, 6B and 6C illustrate a procedure for forming an image according to a first example and advantages thereof.
Figure 6B:
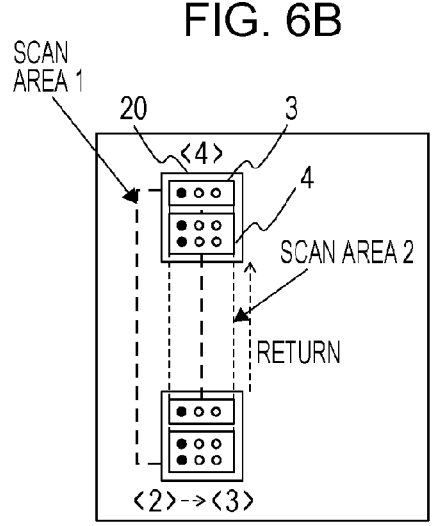
Figure 6C:
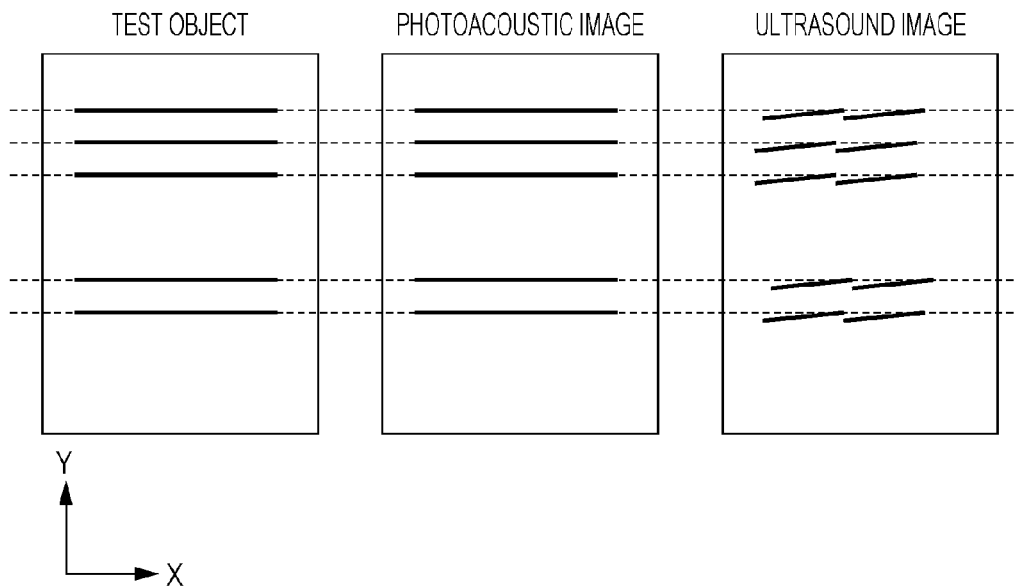

Next, the actual movement of the carriage 20 and the actual image acquisition timing will be described with reference to FIGS. 6A and 6B. In FIGS. 6A and 6B, the carriage 20 is shown without the light source 5. First, during the outbound scan from position <1> toward position <2> (FIG. 6A), the ultrasound probe 3 radiates ultrasound towards the test object 19 and the light source 5 radiates light towards the test object 19. Then, a reflected wave of the ultrasound radiated to the test object 19 and an acoustic wave generated in the test object 19 irradiated with the light are received, whereby an ultrasound image and a photoacoustic image are sequentially acquired. The linear scanning direction of the ultrasound probe 3 in this case is the X direction (i.e., positive direction of the X-axis), as shown in FIG. 6A, similar to FIGS. 3A to 3C described above. After traveling along one line in the scan area and reaching position <2>, the carriage 20 is slid sideways so as to be moved to position <3>. Subsequently, in the return scan from position <3> toward position <4> (FIG. 6B), only the light radiation from the light source 5 is performed. Then, an acoustic wave generated in the test object 19 is received, whereby a photoacoustic image alone is acquired. This series of operation is sequentially repeated in the outbound scan from position <5> toward position <6> and in the return scan from position <7> toward position <8>, whereby both a photoacoustic image and an ultrasound image are acquired in the outbound scan and a photoacoustic image alone is acquired in the return scan. By repeating these steps, the entire area is scanned back and forth in a reciprocating manner, whereby an image of the entire area is acquired. Accordingly, since the ultrasound image is distorted (inclined) in a fixed direction, such distortion becomes unnoticeable, whereby the consistency between the photoacoustic image and the ultrasound image is improved (FIG. 6C). If this inclination in the ultrasound image is to be corrected, the inclination can be corrected by a simple process since the image is inclined uniformly in one direction.

In the case where an ultrasound image is to be acquired by using a reflected wave received only during the outbound scan or the return scan, as in the first example, the sliding distance in the lateral direction (e.g. sliding distance from position <2> to position <3>) is preferably set within a range by which an image of the area to be image-captured can be formed uniformly even with an ultrasound image acquired by using a reflected wave received only during the outbound scan or the return scan of the reciprocating scan process. In the first example, the carriage 20 is slid sideways by 10 mm. The width of a linear scan area of an ultrasound image is set to about 25 mm so that the image can be acquired uniformly.

The ultrasound image and the photoacoustic image respectively re-formed (acquired) by the U-signal processor 9 and the P-signal processor 10 are combined with each other by the controller 12. In the first example, the two images are combined in a side-by-side arrangement in view of the positional relationship therebetween. The combined image data is displayed on the image display unit 13 formed of a liquid-crystal display (FIG. 6C).

In the first example, the uniformity of the ultrasound image is improved in the entire image capture area, and the consistency between the ultrasound image and the photoacoustic image is improved, as compared with a case where an ultrasound image is acquired in both the outbound scan and the return scan.

Second Example

Figure 5:
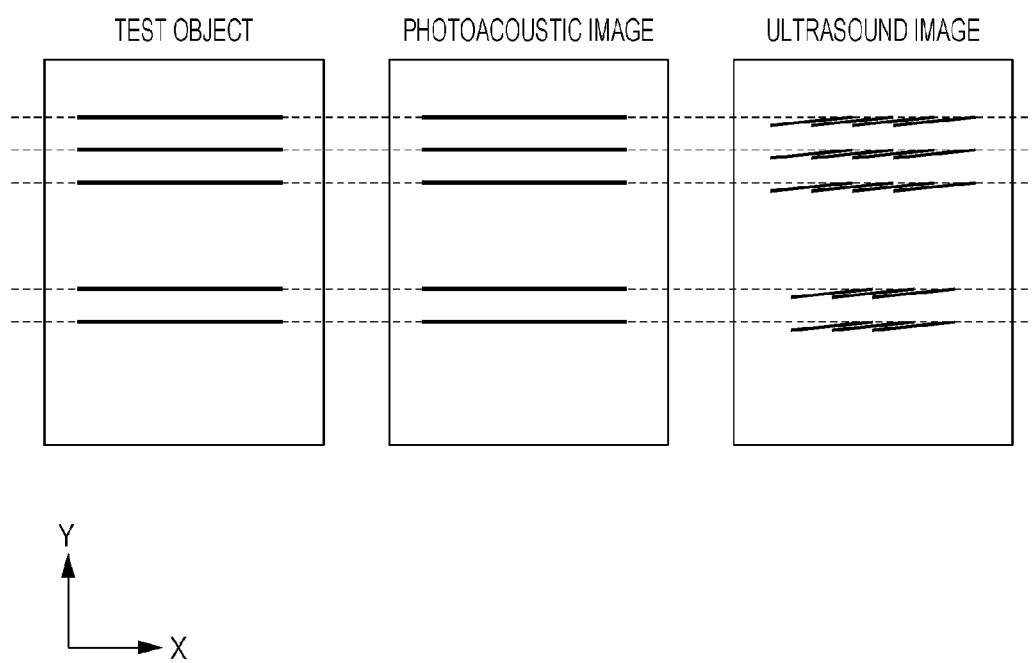
FIG. 5 illustrates a procedure for forming an image according to a second example and advantages thereof.

A second example differs from the first example in that ultrasound is transmitted to the test object 19 from the ultrasound probe 3 in both the outbound scan and the return scan of the reciprocating scan process and that the linear scanning direction of the ultrasound probe 3 is reversed between the outbound scan and the return scan. Specifically, the linear scan is performed in the X direction (i.e., positive direction of the X-axis) shown in FIGS. 6A to 6C in the outbound scan, as in the first example, and the linear scan is performed in the opposite direction in the return scan. Other points, that is, the configuration and the basic operation of the apparatus, are the same as those in the first example. Accordingly, in the second example, an ultrasound image and a photoacoustic image can be acquired from the test object 19 shown in FIG. 5, so that the uniformity of the ultrasound image is improved in the entire image capture area, and the consistency between the ultrasound image and the photoacoustic image is improved, as compared with a case where an ultrasound image is acquired without changing the linear scanning direction between the outbound scan and the return scan.

Furthermore, since data acquired from the same position increases, as compared with the case of the first example, the S/N ratio of the image is improved.

Although the above description relates to a case where the radiation method for radiating ultrasound from the ultrasound probe 3 to the test object 19 is varied between the outbound scan and the return scan of the reciprocating scan process in the above examples, the method for acquiring an ultrasound image may alternatively be varied between the outbound scan and the return scan of the reciprocating scan process. Specifically, in the U-signal processor 9 serving as an ultrasound-image acquisition unit, the method for acquiring an ultrasound image may be varied between a second electric signal converted from a reflected wave received during the outbound scan and a second electric signal converted from a reflected wave received during the return scan. More specifically, an ultrasound image may be acquired by using only one of the second electric signal converted from the reflected wave received during the outbound scan and the second electric signal converted from the reflected wave received during the return scan. In this case, the transmission controller 8 serving as an ultrasound controller can suppress distortion of the ultrasound image in one direction without changing the operation of the ultrasound probe 3 between the outbound scan and the return scan, thereby achieving advantages similar to those in the first example.

Furthermore, in addition to the improvement of the consistency between the photoacoustic image and the ultrasound image, the ultrasound image itself is also improved in the present invention. Specifically, because the ultrasound probe 3 radiates ultrasound towards the test object 19 based on different radiation methods between the outbound scan and the return scan of the reciprocating scan process, the image is distorted uniformly in one direction, as compared with a case where the radiation method is not varied, whereby the image is improved. Moreover, if the acquired image is to be corrected, the correcting process can be simplified since the image is distorted uniformly in one direction. Likewise, the method for acquiring an ultrasound image may be varied between the outbound scan and the return scan of the reciprocating scan process. Specifically, in the U-signal processor 9 serving as an ultrasound-image acquisition unit, the method for acquiring an ultrasound image may be varied between a second electric signal converted from a reflected wave received during the outbound scan and a second electric signal converted from a reflected wave received during the return scan. More specifically, an ultrasound image may be acquired by using only one of the second electric signal converted from the reflected wave received during the outbound scan and the second electric signal converted from the reflected wave received during the return scan. Accordingly, since the image becomes distorted uniformly in one direction, as in the above-described case, the image is improved. Moreover, if the acquired image is to be corrected, the correcting process can be simplified since the image is distorted uniformly in one direction. In this case, since the transmission controller 8 serving as an ultrasound controller does not need to change the operation of the ultrasound probe 3 between the outbound scan and the return scan, operation control of the apparatus can be simplified.

According to the present invention, the consistency between the photoacoustic image and the ultrasound image is improved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-126381 filed Jun. 1, 2012, which is hereby incorporated by reference herein in its entirety.

What is claimed is:

1. A test-object-information acquisition apparatus comprising:
    a light radiating unit configured to radiate light onto a test object;
    a first probe configured to receive an acoustic wave generated in the test object in response to the test object being irradiated with the light from the light radiating unit and converts the acoustic wave into a first electric signal;
    a second probe that includes a plurality of conversion elements arranged in a first direction, and configured to radiate an ultrasound beam towards the test object, to receive a reflected wave of the ultrasound beam from the test object, and to convert the reflected wave into a second electric signal;
    an ultrasound controller configured to control the second probe to radiate the ultrasound beam toward the test object;
    a scanning unit configured to cause the light radiating unit, the first probe, and the second probe to perform a reciprocating scan process across the test object by moving the light radiating unit, the first probe, and the second probe back and forth in a second direction that is different from the first direction;
    a photoacoustic-image acquisition unit configured to acquire a photoacoustic image on the basis of the first electric signal;
    an ultrasound-image acquisition unit configured to acquire an ultrasound image on the basis of the second electric signal, wherein the ultrasound controller is further configured to cause the plurality of conversion elements to linearly scan the ultrasound beam along the first direction, and to vary a linear scanning direction to be different between the forward scan and the backward scan of the reciprocating scan process; and
    a controller configured to correct the acquired ultrasound image.

2. The test-object-information acquisition apparatus according to claim 1, wherein the first probe includes a plurality of conversion elements.

3. The test-object-information acquisition apparatus according to claim 2, wherein the conversion elements are capacitance-type conversion elements.

4. The test-object-information acquisition apparatus according to claim 2, wherein the scanning unit performs the reciprocating scan process at the plurality of positions in such a way as to perform the reciprocating scan processes to regions overlapping each other in the first direction.

5. The test-object-information acquisition apparatus according to claim 1, wherein the light radiating unit includes a laser configured to emit pulsed light.

6. The test-object-information acquisition apparatus according to claim 1, further comprising a support member that supports the test object.

7. The test-object-information acquisition apparatus according to claim 6, wherein the support member is composed of quartz glass, polymethylpentene polymer, polycarbonate, or acrylic.

8. The test-object-information acquisition apparatus according to claim 6, wherein the reciprocating scan process is performed along the support member.

9. The test-object-information acquisition apparatus according to claim 1, further comprising a carriage to which the light radiating unit, the first probe, and the second probe are integrally secured,
    wherein the scanning unit causes the carriage to perform the reciprocating scan process.

10. The test-object-information acquisition apparatus according to claim 1, wherein the scanning unit performs the reciprocating scan process at a plurality of positions in the first direction.

11. The test-object-information acquisition apparatus according to claim 1, wherein the photoacoustic-image acquisition unit acquire a photoacoustic image during the forward scan and the backward scan of the reciprocating scan process.

12. The test-object-information acquisition apparatus according to claim 1, wherein the controller combines the ultrasound image, the distortion of which has been corrected, and the photoacoustic image.

13. A test-object-information acquisition apparatus, comprising:
    a light radiating unit configured to radiate light onto a test object;
    a first probe configured to receive an acoustic wave generated in the test object in response to the test object being irradiated with the light from the light radiating unit and converts the acoustic wave into a first electric signal;
    a second probe that includes a plurality of conversion elements arranged in a first direction, and configured to radiate an ultrasound beam towards the test object, to receive a reflected wave of the ultrasound beam from the test object, and to convert the reflected wave into a second electric signal;
    an ultrasound controller configured to control the second probe to radiate the ultrasound beam toward the test object;
    a scanning unit configured to cause the light radiating unit, the first probe, and the second probe to perform a reciprocating scan process across the test object by moving the light radiating unit, the first probe, and the second probe back and forth in a second direction that is different from the first direction;
    a photoacoustic-image acquisition unit configured to acquire a photoacoustic image on the basis of the first electric signal; and an ultrasound-image acquisition unit configured to acquire an ultrasound image on the basis of the second electric signal;

wherein the ultrasound controller is configured to make the second probe radiate the ultrasound beam to the test object during only one of the forward scan and the backward scan of the reciprocating scan process;

further comprising a controller configured to correct distortion of the acquired ultrasound image.

14. A test-object-information acquisition method for acquiring a photoacoustic image by receiving an acoustic wave generated in a test object by radiating light to the test object and acquiring an ultrasound image by receiving a reflected wave reflected from the test object after radiating an ultrasound beam to the test object using a plurality of conversion elements arranged in a first direction, the method comprising:

a step of irradiating light emitted by a light radiating unit onto the test object;

a step of acquiring a photoacoustic image in response to radiating the light to the test object while scanning the light across the test object in a reciprocating manner and then receiving the acoustic wave therefrom; and a step of acquiring the ultrasound image by radiating the ultrasound beam to the test object while scanning the ultrasound beam across the test object in a reciprocating manner and then receiving the reflected wave therefrom, wherein the radiation of the ultrasound beam performed while scanning the ultrasound beam across the test object in a reciprocating manner is performed based on different radiation methods between an outbound scan and a return scan in the step of acquiring the ultrasound image.

15. The test-object-information acquisition method according to claim 14, further comprising a step of combining the ultrasound image, the distortion of which has been corrected, and the photoacoustic image.

16. A test-object-information acquisition method for acquiring a photoacoustic image receiving an acoustic wave generated in a test object by radiating light to the test object and acquiring an ultrasound image by receiving a reflected wave reflected from the test object after radiating an ultrasound beam to the test object using a plurality of conversion elements arranged in a first direction, the method comprising:

a step of acquiring a photoacoustic image by receiving the acoustic wave while scanning and radiating light across the test object back and forth in a reciprocating manner in a second direction that is different from the first direction; and a step of acquiring the ultrasound image by radiating the ultrasound beam to the test object using a plurality of conversion elements while scanning the ultrasound beam across the test object in a reciprocating manner and then receiving the reflected wave therefrom, wherein in the step of acquiring the ultrasound image, the ultrasound beam is radiated to the test object during only one of the forward scan and the backward scan of the reciprocating scan, and further wherein the test-object-information acquisition method further comprises a step of correcting distortion of the acquired ultrasound image.

17. The test-object-information acquisition method according to claim 16, further comprising a step of combining the ultrasound image, the distortion of which has been corrected, and the photoacoustic image.

* * * * *